United States Patent [19]

Chevallet et al.

[11] Patent Number: 5,342,527
[45] Date of Patent: Aug. 30, 1994

[54] METHOD FOR THE CALIBRATION OF A PAIR OF SENSORS PLACED IN A DIALYSIS CIRCUIT

[75] Inventors: Jacques Chevallet, Serezin Du Rhone; Bernard Bene, Irigny, both of France

[73] Assignee: Hospal Industrie, France

[21] Appl. No.: 82,928

[22] Filed: Jun. 29, 1993

[30] Foreign Application Priority Data

Jun. 30, 1992 [FR] France .................. 9208287

[51] Int. Cl.⁵ .................. B01D 61/32; G01F 25/00
[52] U.S. Cl. .................. 210/646; 73/3; 210/85; 210/97; 210/321.65; 210/739; 364/571.01
[58] Field of Search .................. 210/645, 646, 739, 85, 210/97, 102, 137, 142, 252, 321.65, 321.71, 929; 73/3; 364/510, 571.01-571.08

[56] References Cited

U.S. PATENT DOCUMENTS 5,111,683  5/1992  Fond .................. 73/3

FOREIGN PATENT DOCUMENTS 0298587  1/1989  European Pat. Off. .

Primary Examiner—Robert A. Dawson
Assistant Examiner—Sun Uk Kim
Attorney, Agent, or Firm—Finnegan, Henderson, Farabow, Garrett & Dunner

[57] ABSTRACT

Disclosed is a method for the calibration of a pair of sensors placed in a dialysis circuit. The method includes performing at least one step for determining an auxiliary calibration coefficient for the intake sensor, performing at least one step for determining an auxiliary calibration coefficient for the outlet sensor, and in determining on the basis of at least one auxiliary calibration coefficient, a new calibration coefficient for the two sensors.

10 Claims, 3 Drawing Sheets

FIG. 5

| STAGE | DURATION | CALIBRATION COEFFICIENT | AUXILIARY COEFFICIENT |
|---|---|---|---|
| $Phe_1$ | $Te_1$ | $Ko = \dfrac{Keo}{Kso}$ | $Ke_1 = \dfrac{Fe1}{Fa1}$ |
| $Phs_2$ | $Ts_2$ | $K1 = \dfrac{Ke1}{Kso}$ | $Ks_2 = \dfrac{Fs2}{Fa2}$ |
| $Phe_3$ | $Te_3$ | $K2 = \dfrac{Ke1}{Ks2}$ | $Ke_3 = \dfrac{Fe3}{Fa3}$ |
| $Phs_4$ | $Ts_4$ | $K3 = \dfrac{Ke3}{ks2}$ | $Ks_4 = \dfrac{Fs4}{Fa4}$ |
| " " | " " | " " | " " |
| $Phei$ | $Tei$ | $K_{i-1} = \dfrac{Ke(i-2)}{Ks(i-1)}$ | $Kai = \dfrac{Fei}{Fai}$ |
| $Phsj$ | $Tsj$ $avesj = i+1$ | $K_i = \dfrac{Kei}{Ks(i-1)}$ | $Ksj = \dfrac{Fsj}{Faj}$ |

METHOD FOR THE CALIBRATION OF A PAIR OF SENSORS PLACED IN A DIALYSIS CIRCUIT

BACKGROUND OF THE INVENTION

1. Field of the Invention

The present invention concerns the measurement of physical quantities of a dialysis liquid circulating in a haemodialyzer of an artificial kidney. More particularly, the invention concerns the calibration of sensors used for measuring the chemical or physical quantities of the dialysis liquid. The invention finds a particularly advantageous application for measuring the flow rate of the dialysis liquid circulating in the haemodialyzer of an artificial kidney.

2. Description of the Related Art

In a conventional way for measuring the flow rate of a dialysis liquid circulating in a haemodialyzer of an artificial kidney, an artificial kidney comprises a haemodialyzer with two compartments separated by a membrane, where one compartment is connected to a dialysis liquid circuit, while the other compartment is connected to a patient by means of an extracorporeal blood circuit. At the intake and outlet of the haemodialyzer, the dialysis liquid circuit is provided with flowmeters generating an electric pulse at the passing of a specified fraction of dialysis liquid.

During a dialysis liquid session, the excess liquid present in the blood ultrafilters through a membrane because of the pressure gradient exerted on either side of the membrane. As a predicate to such a session, it is necessary to calibrate the flowmeters, for which the haemodialyzer is bypassed, so that an identical flow of dialysis liquid circulates in the two flowmeters. This calibration stage involves measuring the calibration frequencies of each flowmeter by counting the number of pulses during a given duration time, so as to define the response factor. The response factor is the relation existing between a measurement frequency and a specified flow of dialysis liquid. Such a calibration stage makes it possible to partially correct the intrinsic errors of the flowmeter, and even to use flowmeters of a different kind.

The calibration of the flowmeters results from experimental measurements, and therefore is vitiated by a certain error which systematically affects the results of subsequent measurements. Thus, it appears indispensable to reduce the accidental measurement errors as far as possible, which are likely to appear in the course of the calibration stage, so as to obtain a maximum measurement accuracy for the determination of the ultrafiltrate withdrawn from the patient's blood.

To try to reduce the magnitude of the measurement errors, the prior art generally proposes to proceed with a calibration stage extending over a fairly long period. Moreover, the Patent Application EP A 0298 587 proposes a method which attempts to limit the errors in flow rate measurements, particularly during the calibration stage of flowmeters equipping a haemodialyzer. This document proposes to mount one pair of flowmeters upstream from the haemodialyzer and another pair downstream from the haemodialyzer in series in the dialysis liquid circuit. During the calibration stage, the haemodialyzer is bypassed so that the four flowmeters are again placed in series. The frequencies of the flowmeters are measured, and the calibration is considered to be valid if the differences between the measured frequencies fall within a specified range of values.

The main drawback of the method described above lies in that the accuracy of the measurements depends directly on the time of acquisition during which the pulses are counted. Thus, to reach a high accuracy, it is necessary to increase the acquisition time of the measurements in a prohibitive way.

Moreover, it has been shown in practice that the flowmeters are subject to a measurement drift in the course of a dialysis session whose duration generally reaches four hours. It then becomes necessary to proceed with calibrations during the dialysis session to eliminate this error, which reduces the efficiency of the dialysis because of the long duration of the calibration stage. Moreover, the doubling up of the flowmeters increases the costs of operating such a procedure.

To resolve the drawbacks set out above, U.S. Pat. No. 5,111,683 issued to Fond has proposed a calibration method making it possible to obtain a high measurement accuracy that is independent of the calibration time. The calibration time necessary for the implementation of the method may be limited to a minimum duration without, however, affecting the measurement accuracy, since the errors liable to occur during this calibration period are eliminated by the proposed calibration method. This stage of calibrating the flowmeters, during which the haemodialyzer is bypassed, may be carried out during a dialysis session because of the short time necessary to undertake this calibration.

Of course, if the number of calibrations becomes high with an aim to increasing the accuracy of the measurements, the sum total of the periods necessary for successive calibrations leads to a considerable calibration time. This overall calibration time, during which the haemodialyzer is bypassed, leads to a reduction in the efficiency of the dialysis session. Therefore, a compromise must be made between the efficiency of the dialysis session and the accuracy of the measurements, without neglecting the reliability necessary to reveal an irregularity in the flowmeters as quickly as possible.

Hence, there is a need for a calibration method for flowmeters that makes it possible to obtain a high measurement accuracy throughout the dialysis session, and for achieving an optimum efficiency for this session by overcoming the need for bypassing the haemodialyzer during the session.

SUMMARY OF THE INVENTION

An object of the invention is a calibration method for sensors to satisfy the need set out above.

Another object of the invention is a calibration method offering a high reliability in revealing possible errors liable to occur in the sensors in the course of a dialysis session.

To attain the objectives set out above, the invention comprises a method to calibrate a pair of sensors, where one of the sensors is mounted at the intake and the other at the outlet of a dialysis circuit intended to be connected to a haemodialyzer. The method comprises carrying out an initial stage of calibrating the sensors during which the haemodialyzer is bypassed so as to determine the response factor of each sensor and to define an initial calibration coefficient making it possible to obtain an identical measurement value for each sensor, and in obtaining at least one correction stage of the initial calibration coefficient in the course of an operating session of the haemodialyzer.

The invention further includes a method comprising obtaining at least one stage for determining an auxiliary calibration coefficient for the intake sensor, the method being constituted by ensuring that an auxiliary sensor of the same kind as the intake and outlet sensors is placed in series with the intake sensor; defining the response factors for the intake and auxiliary sensors; and defining the auxiliary calibration coefficient for the intake sensor, making it possible to obtain the same measurement value for the intake and auxiliary sensors. The method further includes obtaining at least one stage for determining an auxiliary calibration coefficient for the outlet sensors constituted by ensuring that the outlet sensor is placed in series with the auxiliary sensor; defining the response factors for the outlet and auxiliary sensors; and defining the auxiliary calibration coefficient for the outlet sensor, making it possible to obtain the same measurement value for the outlet and auxiliary sensors. The method further comprises determining on the basis of the auxiliary calibration coefficient or coefficients, a new calibration coefficient for the two sensors.

Various other characteristics will emerge from the description given below with reference to the attached drawings.

BRIEF DESCRIPTION OF THE DRAWINGS

FIG. 5 shows a table describing the calibration method according to the invention.

DETAILED DESCRIPTION OF THE PREFERRED EMBODIMENT

Figure 1:
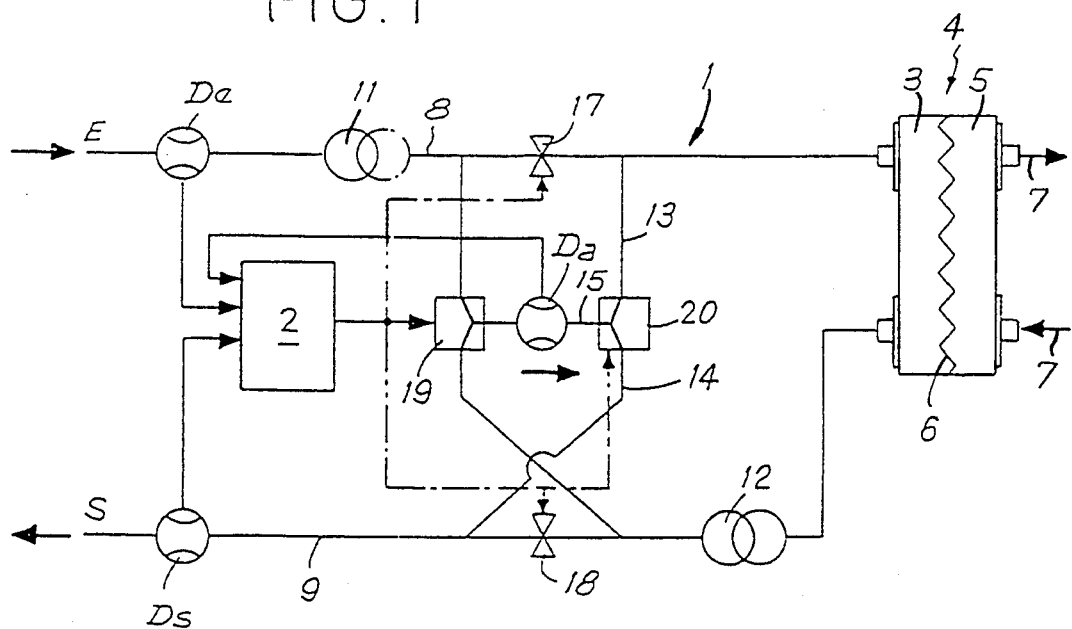
FIG. 1 is a diagram of an artificial kidney for operating the calibration method according to the invention.

The kidney represented in FIG. 1 is adapted to ensure the calibration of a pair of sensors De, Ds which are intended to ensure the measurement of physical or chemical quantities of a dialysis liquid circulating in a circuit 1. By way of example only and as illustrated in the Figures, the sensors De, Ds constitute flowmeters connected to a measurement and control device 2, whose function will emerge more precisely below.

The circuit 1 is connected to a first compartment 3 of a haemodialyzer 4. Haemodialyzer 4 includes a second compartment 5 separated from the first compartment 3 by a membrane 6, and connected to a patient via an extracorporeal blood circuit 7. The circuit 1 comprises an intake or upstream line 8 fitted with the intake flowmeter De and connected, on one side, via its inlet E to a source of dialysis liquid (not shown) and, on the other side, to an inlet of the compartment 3. The circuit 1 also comprises an outlet or downstream line 9 equipped with the outlet flowmeter Ds and connected to an outlet of the compartment 3 on one side and on another side to evacuation or recycling means (not shown) via its outlet S. In the example illustrated, the intake line 8 and the outlet line 9 are provided with means for displacing the dialysis liquid, such as the pumps 11 and 12 respectively.

Figure 2:
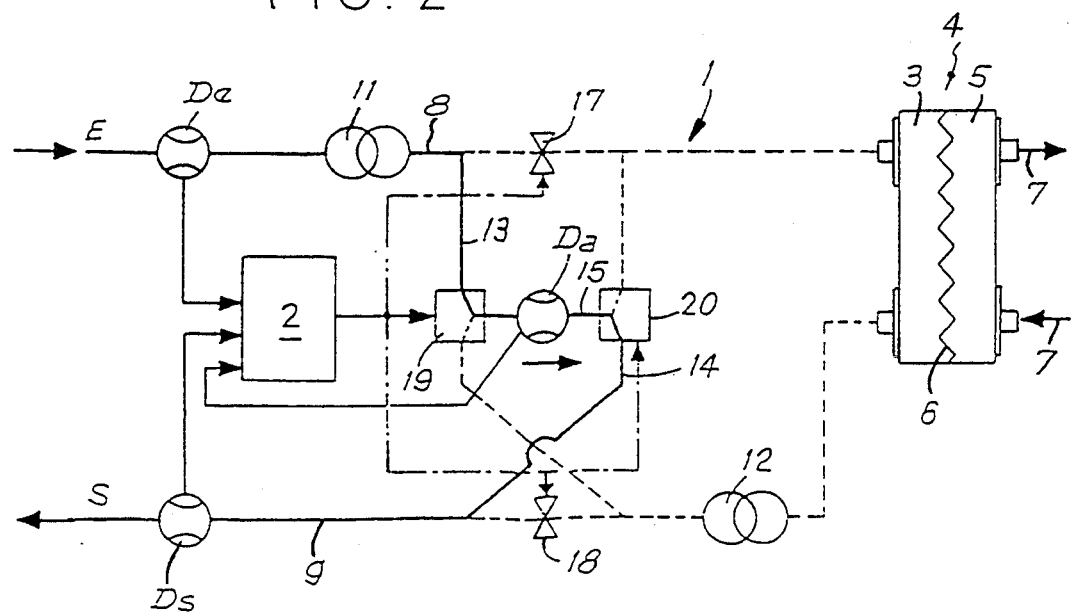
FIG. 2 is a diagram similar to FIG. 1 showing the path of the dialysis liquid through the artificial kidney during initial calibration.

To operate the calibration method according to the invention, the dialysis liquid circuit 1 includes an upstream branch 13 for bypassing the intake line 8, and a downstream branch 14 for bypassing the outlet line 9. The bypass branches 13, 14 include a common portion 15 wherein there is mounted an auxiliary sensor Da, such as a flowmeter in the example illustrated, connected to the device 2. The circuit 1 is provided with obturating means permitting the circulation of the dialysis liquid, either through the three flowmeters De, Da, Ds mounted in series, while the haemodialyzer is placed in the bypass mode (FIG. 2), or through the upstream branch 13 (FIG. 3), or through the downstream branch 14 (FIG. 4).

By way of example, the obturating means are formed by a stop valve 17 placed in the upstream line 8, between the flowmeter De and the haemodialyzer 4. The obturating means also includes a stop valve 18 mounted in the downstream line 9, between the flowmeter Ds and the haemodialyzer 4. The obturating means also include valves 19, 20 placed on either side of the common portion 15 and connected to the bypass branches 13, 14. Bypass branches 13, 14 are connected respectively downstream and upstream from the stop valves 17, 18.

The obturating means 17, 18, 19, 20 are preferably controlled by the measurement and control device 2 which, in order to operate the method according to the invention, includes means for calibrating the intake sensor De and outlet sensor Ds.

Prior to a dialysis session, an initial stage of calibrating the flowmeters De, Ds is carried out, so as to obtain an identical measurement value for each sensor, during a circulation in the latter of the same flow value of the dialysis liquid. To obtain this initial calibration and in reference to FIG. 2, the valves 17 and 18 are closed, while the valves 19 and 20 are actuated to permit a circulation of the dialysis liquid through a portion of the upstream line 8, a portion of the bypass branch 13, the common portion 15, a portion of the bypass branch 14, and a portion of the downstream line 9. The sensors De, Da, Ds are thus placed in series, while the haemodialyzer 4 is bypassed in relation to the circuit 1. During this calibration stage, the flow of the liquid circulating in the three flowmeters is strictly identical to the extent that the circuit thus formed does not have any point of loss or gain of the dialysis liquid.

The device 2 which ensures the acquisition of the data coming from the sensors De, Da, Ds determines respectively the response factors Feo, Fao, Fso. Response factors Feo, Fao, Fso are the relation existing between an electric signal delivered by the sensor and a flow rate of the dialysis liquid. The device 2 then defines an auxiliary calibration coefficient keo for the intake sensor De and an auxiliary calibration coefficient kso for the outlet sensor Ds.

Each auxiliary calibration coefficient keo, kso is formed, for example, by the ratio between the response factors Feo, Fao of the sensors De, Da, and the response factors Fso and Fao of the sensors Ds and Da respectively, so that keo =Feo/Fao and kso =Fso/Fao. The device 2 then determines an initial calibration coefficient Ko which can be, for example, the ratio between the auxiliary calibration coefficient keo and kso, such that Ko =keo/kso.

The device 2 also determines an initial calibration coefficient Ko' corresponding to the ratio between the response factors Feo and Fso of the sensors De, Da, so that Ko'=Feo/Fso. The device 2 compares the coefficient Ko and Ko', and if a difference appears between the two calculated values, the device 2 can emit a warning signal signifying a leak at the level of the valves 17, 18 or an incorrect count. If the coefficients Ko and Ko' have substantially identical values, the device 2 validates the initial calibration coefficient Ko, which will make it possible to correct the measurements of the flow rate carried out by the flowmeters during the dialysis session.

The method according to the invention permits the calibration of the flowmeters during the dialysis session that follows the initial calibration stage. During such a dialysis session, one proceeds with at least one stage Phei, Phsj, respectively, for determining a new auxiliary calibration coefficient for the intake sensor De and the outlet sensor Ds.

Figure 3:
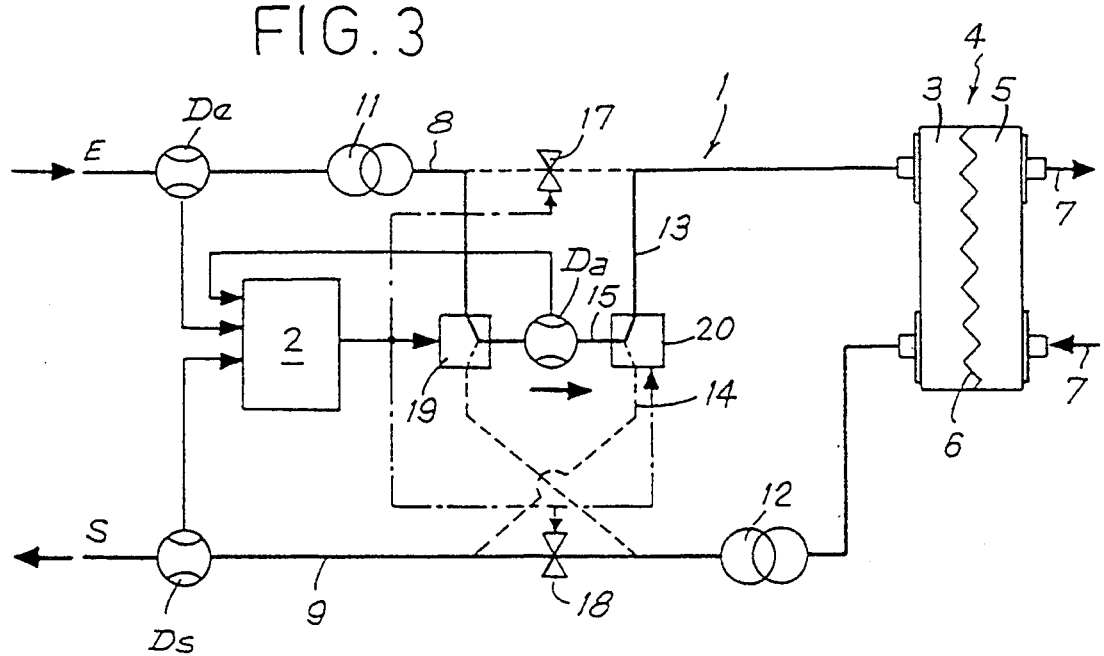
FIG. 3 is a diagram similar to FIG. 1 showing the path of the dialysis liquid through the artificial kidney during calibration of the intake sensor.
Figure 4:
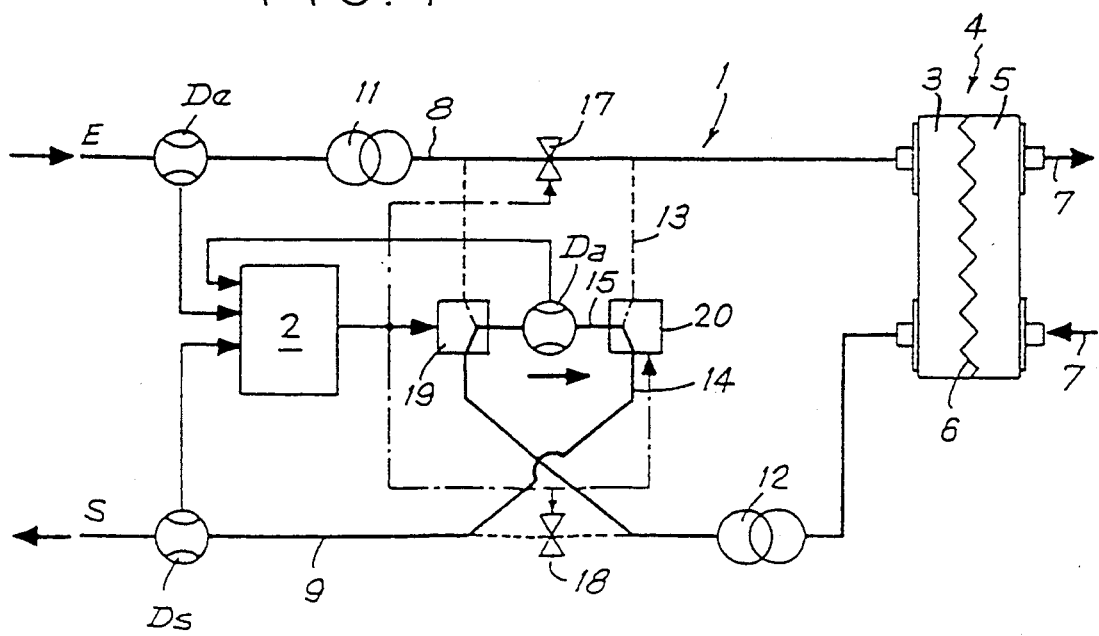
FIG. 4 is a diagram similar to FIG. 1 showing the path of the dialysis liquid through the artificial kidney during calibration of the outlet sensor.

As apparent in FIG. 3, the stage $Phe_1$ of determining a new auxiliary calibration coefficient for the intake sensor De, having a duration $Te_1$, lies in closing the valve 17 and opening the valve 18 and in actuating the valves 19 and 20 so that the dialysis liquid circulates in the upstream line 8 placed in series with the upstream bypass branch 13, and in the downstream line 9. The auxiliary sensor Da is thus placed in series with the intake sensor De. Insofar as the sensors De and Da are traversed by the same flow of dialysis liquid, one can proceed with a new calibration of the sensor De in comparison with the sensor Da. For this purpose, the response factors $Fe_1$ and $Fa_1$ of the sensors De and Da are again determined by the device 2, so as to determine a new auxiliary coefficient $ke_1$ such that $ke_1 = Fe_1/Fa_1$.

This new coefficient $ke_1$ is intended to replace in the calibration coefficient Ko, the auxiliary coefficient keo of the sensor De which has been defined during the initial calibration stage. A new calibration coefficient $k_1$ is defined such that $K_1 = ke_1/kso$ (FIG. 5). It should be noted that the initial coefficient Ko is used during this stage $Phe_1$ of duration $Te_1$, while the new coefficient $K_1$ is taken into account for the continuation of the dialysis session, $Phs_2$.

The stage $Phe_1$ is followed by a stage $Phs_2$ of duration $Ts_2$ intended to ensure the determination of a new auxiliary calibration coefficient for the outlet sensor Ds. As shown in FIG. 4, during this stage the valve 17 is open, and the valve 18 is closed, while the valves 19 and 20 are actuated in such a way that the dialysis liquid circulates in the downstream bypass branch 14. Thus, the dialysis liquid circulates in the upstream line 8 and the downstream line 9 placed in series with the bypass branch 14. The auxiliary sensor Da is thus placed in series with the outlet sensor Ds. It should be noted that the bypass branch 14 is connected to the downstream line 9 in such a way that the dialysis liquid circulates in the common portion 15 in a direction that is identical with the passing of the liquid circulating in the branch 13.

During this stage $Phs_2$, response factors $Fs_2$ and $Fa_2$ are determined, respectively, for the sensors Ds and Da by the device 2, to define a new auxiliary coefficient $ks_2$ for the outlet sensor Ds, such that $ks_2 = Fs_2/Fa_2$. This new coefficient $ks_2$ is intended to replace in the calibration coefficient $K_1$ the auxiliary coefficient kso of the sensor Ds which has been defined during the initial calibration stage. A new calibration coefficient $K_2$ is thus defined, with $K_2 = ke_1/ks_2$.

Advantageously, the stages Phei and Phsj of determining the auxiliary coefficient kei, ksj for the intake sensor De and outlet sensor Ds are obtained alternately and successively in the course of a dialysis session, so as to define successive calibration coefficients Ki. It should be noted that in the preceding description, the calibration coefficients Ki are modified when a new auxiliary coefficient kei or ksj is determined. It is envisaged to modify the calibration coefficients Ki only when a new auxiliary coefficient kei and a new auxiliary coefficient ksj are determined at the same time.

Preferably, the stages Phei and Phsj are obtained consecutively. By way of example, it is envisaged that each stage Phei, Phsj for determining an auxiliary coefficient kei, ksj, respectively, is effected during a period Tei = Tsj = 5 minutes. Thus, it is possible to obtain a new calibration coefficient Ki every 5 minutes if the stages are obtained consecutively one after the other.

The calibration method in accordance with the invention can thus be effected throughout the whole duration of the dialysis session without affecting the efficiency of the session, insofar as the calibration is effected without putting the haemodialyzer into the bypass mode. Thus, one may proceed with many calibrations in the course of the dialysis session so as to ensure a good accuracy of the measurements throughout the session. Moreover, it should be noted that the calibration of the intake flowmeter De is effected with fresh dialysis liquid, while that of the outlet flowmeter Ds is effected with used dialysis liquid, so that the calibration and measurement stages are effected in the same conditions.

Advantageously, each auxiliary calibration coefficient kei, ksj is determined on the basis of the average of a series of elementary auxiliary coefficients determined in the course of a corresponding correction stage. In the example taken above, it is envisaged that one proceeds with the average of ten elementary auxiliary coefficients determined during the correction stage of duration Tei = Tsj = 5 minutes.

According to the invention, the auxiliary coefficients kei, ksj of the sensors De, Ds are compared respectively with the corresponding auxiliary coefficients determined in the course of a preceding stage of the same kind, so as to allow a possible defect appearing in the sensors De or Ds to be detected. A warning signal is, of course, delivered when the difference between these values exceeds a given threshold. It should be noted that the use of a single auxiliary flowmeter Da whose data are capable of being transmitted to a protective system independent of the measurement and control device of the kidney machine makes it possible to obtain an optimum reliability regarding the values delivered by the flowmeters.

Moreover, it should be noted that the calibration method in accordance with the invention can be used in all types of dialysis circuits 1 equipping a haemodialyzer. For example, the calibration method according to the invention can be applied to the flowmeters of a dialysis liquid whose flow rate is kept constant at the intake and at the outlet by the pump 12.

It should also be borne in mind that the calibration method according to the invention is advantageously operated by programming means installed inside the measurement and control device 2.

The invention is not limited to the examples that have been described and represented since various modifications may be applied thereto without departing from its scope.

What is claimed is:

1. A method for calibrating intake and outlet sensors in a dialysis circuit including a haemodialyzer having an intake side and an outlet side, the intake sensor mounted at an intake portion of the circuit on the intake side of the haemodialyzer, and the outlet sensor mounted at an outlet portion of the circuit on the outlet side of the haemodialyzer, the method comprising the steps of:

controlling flow of liquid to bypass the haemodialyzer, determining an initial response factor for each of the intake and outlet sensors, and calculating an initial calibration coefficient;

correcting the initial calibration coefficient, the step of correcting including performing at least one of a first step and a second step, the first step including placing an auxiliary sensor of a same type as the intake and outlet sensors in series with the intake sensor, controlling the flow of liquid to flow through the haemodialyzer, determining first response factors for the intake and auxiliary sensors, and calculating an intake auxiliary calibration coefficient for the intake sensor based on the first response factors for the intake and auxiliary sensors;

the second step including placing the outlet sensor in series with the auxiliary sensor, controlling the flow of liquid to flow through the haemodialyzer, determining second response factors for the outlet and auxiliary sensors, and calculating an outlet auxiliary calibration coefficient for the outlet sensor based on the second response factors for the outlet and auxiliary sensors; and updating the initial calibration coefficient based upon at least one of the intake auxiliary calibration coefficient and the outlet auxiliary calibration coefficient.

2. The method according to claim 1, wherein the correcting step includes alternating successively the first and second steps.

3. The method according to claim 2, wherein after the first step, the calculated intake auxiliary calibration coefficient replaces any previously calculated intake auxiliary calibration coefficients, and after the second step, the calculated outlet auxiliary calibration coefficient replaces any previously calculated outlet auxiliary calibration coefficients.

4. The method according to claim 1, wherein the intake and outlet auxiliary calibration coefficients are determined based on an average of a series of elementary auxiliary coefficients determined during the first and second steps, respectively.

5. The method according to claim 1, wherein the step of controlling flow of liquid to bypass the haemodialyzer includes placing the intake sensor, the auxiliary sensor, and the outlet sensor in series, thereby defining the intake auxiliary calibration coefficient between the intake and auxiliary sensors, and defining the outlet auxiliary calibration coefficient between the outlet and auxiliary sensors, the initial calibration coefficient being calculated based upon the intake and outlet auxiliary calibration coefficients.

6. The method according to claim 5, wherein the step of controlling flow of liquid to bypass the haemodialyzer includes defining a checking coefficient corresponding to a ratio between the initial response factors, comparing the initial calibration coefficient to the checking coefficient, and validating the initial calibration coefficient only when values of the initial calibration coefficient and checking coefficient are substantially identical.

7. The method according the claim 1, wherein the step of updating the initial calibration coefficient includes calculating a new calibration coefficient by a ratio of the intake auxiliary calibration coefficient and the outlet auxiliary calibration coefficient.

8. The method according to claim 1, further comprising, comparing, after the first step, the intake auxiliary calibration coefficient with an intake auxiliary calibration coefficient determined in a preceding run, and delivering a warning signal when a difference between the compared intake auxiliary calibration coefficients exceeds a given threshold;

and after the second step, comparing the outlet auxiliary calibration coefficient with an outlet auxiliary calibration coefficient determined in a preceding run, and delivering a warning signal when a difference between the compared outlet auxiliary calibration coefficients exceeds a given threshold.

9. The method according to claim 1, wherein the first and second steps include ensuring that the auxiliary sensor is connected in series with the intake sensor or the outlet sensor, respectively, to ensure that dialysis liquid always circulates in a same direction through the auxiliary sensor.

10. An artificial kidney comprising:
a dialysis liquid circuit including,
an intake line having at least an intake sensor, the intake line for connection to a first compartment of a haemodialyzer;
an outlet line having at least an outlet sensor, the outlet line for connection to an outlet of the first compartment, the first compartment being separated by a semipermeable membrane from a second compartment, the second compartment for connection to a circuit for the extracorporeal circulation of the blood;
means for displacing a dialysis liquid;
a measurement and control device connected to the intake sensor and the outlet sensor and for allowing an initial calibration coefficient to be defined for the intake sensor and the outlet sensor;
an upstream branch connected to the intake line for bypassing a portion of the intake line and a downstream branch connected to the outlet line for bypassing a portion of the outlet line, the upstream and downstream branches having a common portion wherein at least one auxiliary sensor of a same kind as the intake and outlet sensors is mounted;
obturating means controlled by the control device and allowing dialysis liquid to circulate in the upstream or downstream branch;
wherein the control device includes,
means for determining a duration and frequency of correction steps for correcting the initial calibration coefficients;
means for defining, during correction steps, an intake auxiliary calibration coefficient and an outlet auxiliary calibration coefficient for the intake sensor and the outlet sensor, respectively, the intake auxiliary calibration coefficient being determined based on a relation between the auxiliary and intake sensors, and the outlet auxiliary calibration coefficient being determined based on a relation between the auxiliary and outlet sensors; and
means for correcting the initial calibration coefficients by using at least one of the intake auxiliary calibration coefficient or the outlet auxiliary calibration coefficient to result in a new calibration coefficient.

* * * * *